US008518226B1

(12) United States Patent
Backhouse et al.

(10) Patent No.: US 8,518,226 B1
(45) Date of Patent: Aug. 27, 2013

(54) MICROFLUIDIC METHODS FOR THE SEPARATION OF SUPERCOILED DNA

(76) Inventors: Christopher Backhouse, Edmonton (CA); Dammika Manage, Edmonton (CA); Iveta Sosova, Edmonton (CA); Moira Glerum, Edmonton (CA)

( * ) Notice: Subject to any disclaimer, the term of this patent is extended or adjusted under 35 U.S.C. 154(b) by 686 days.

(21) Appl. No.: 12/593,583

(22) PCT Filed: Mar. 31, 2008

(86) PCT No.: PCT/CA2008/000740
§ 371 (c)(1),
(2), (4) Date: Mar. 15, 2010

(87) PCT Pub. No.: WO2008/119191
PCT Pub. Date: Oct. 9, 2008

Related U.S. Application Data

(60) Provisional application No. 60/907,361, filed on Mar. 29, 2007.

(51) Int. Cl.
*G01N 27/447* (2006.01)
(52) U.S. Cl.
CPC ........ *G01N 27/44747* (2013.01); *G01N 27/447* (2013.01)
USPC .......................................... 204/451; 204/450
(58) Field of Classification Search
CPC ...................... G01N 27/447; G01N 27/44747
USPC ........................ 204/450–455; 536/22.1–25.6
See application file for complete search history.

(56) References Cited

PUBLICATIONS

L. Ding, et al., "Analysis of plasmid samples on a microchip", Analytical Biochemistry, vol. 316, No. 1, May 2003, p. 92-102.*
Manage et al. A mircofluidic study of mechanisms in the electrophoresis of supercoiled DNA. Electrophoresis 2008. 29. 2466-2476.
Regtmeier et al. Dielectrophorietic Manipulation of DNA: Separation and Polarizability. Analytical Chemistry. May 15, 2007. vol. 79. No. 10. 3925-3932.
Akerman, Effects of Supercoiling in Electrophoretic Trapping of Circular DNA in Polyacrylamide Gels. Biophysical Journal. Jun. 1998. vol. 74. 3140-3151.
Akerman et al. Electrophoretic capture of circular DNA in gels. Electrophoresis. 2002. 23. 2549-2561.
Cole et al. Enhanced Capacity for Electrophoretic Capture of Plasmid DNA by Agarase Treatment of Agarose Gels. Biomacromolecules. 2000. 1. 771-781.

* cited by examiner

*Primary Examiner* — J. Christopher Ball
(74) *Attorney, Agent, or Firm* — Marsh Fischmann & Breyfogle LLP

(57) ABSTRACT

The present invention provides for a novel method of supercoiled DNA isolation using a microfluidic device. In a preferred embodiment, the supercoiled DNA is a plasmid present in combination with chromosomal DNA. The present invention also provides for a novel method of mitochondrial DNA isolation using a microfluidic device.

33 Claims, 12 Drawing Sheets

FIURE 10

MICROFLUIDIC METHODS FOR THE SEPARATION OF SUPERCOILED DNA

RELATED APPLICATION

This application claims the benefit of U.S. Provisional Application Ser. No. 60/907,361, filed Mar. 29, 2007 filed under 35 U.S.C. 119(e). The entire disclosure of the prior application is hereby incorporated by reference.

INCORPORATION BY REFERENCE

This application incorporates by reference the ASCII Text File Entitled "SequenceListing.txt" created on Apr. 8, 2013 and being 1 kb in size.

FIELD OF THE INVENTION

The present invention pertains to the field of nucleic acid preparation and purification using a microfluidic device.

BACKGROUND OF THE INVENTION

All of the publications, patents and patent applications cited within this application are herein incorporated by reference in their entirety to the same extent as if the disclosure of each individual publication, patent application or patent was specifically and individually indicated to be incorporated by reference in its entirety.

Bacterial plasmids are supercoiled loops of DNA that are typically in the range of thousands of base pairs in length—relatively small compared to the linear bacterial chromosomal DNA (chDNA), which is typically millions of base pairs in length. If the double-stranded DNA of the plasmid DNA (pDNA) loop is nicked, the loop will untwist to form open-circular (OC) loops of DNA. These differences in topology and length give substantially different electrophoretic behaviours. Once purified, pDNA can be used in a wide variety of downstream applications such as cloning, sequencing, PCR, expression of proteins, transfection, and gene therapy. In addition, the rapid and inexpensive development of new plasmid purification methods may also provide an efficient means to test the efficiency of transfections and confirm the existence or absence of given mutations in transfected cell experiments. The preparation of plasmids is therefore a key technology for many applications in the fields of molecular biology, genetics, biochemistry and cell biology.

Among the multitude of plasmid purification methods, the alkaline lysis method is widely used to prepare bacterial plasmids in highly purified form. This method relies on lysing of bacterial cells under alkaline conditions and precipitation of the chDNA. Removal of chDNA through centrifugation allows subsequent purification of the pDNA. Bacterial plasmid mini-preps have been made easier through the availability of commercial kits that provide prepared solutions, although the procedure still takes about an hour. While the speed is faster, these kits considerably increase the per-preparation cost involved. Most importantly, these kits require large amounts of sample and their integration into a lab-on-chip format is problematic in terms of speed, the need for complex fluid manipulations, filtering and centrifuging. While mini-prep methods are commonplace for bacteria and yeast, they are not commonly used for higher eukaryotes, mostly because of the large amounts of material and the expense that would be needed for such an approach.

pDNA molecules can exist either in a supercoiled (SC) conformation, a loop that contains sufficient twists that the DNA bunches into a ball, or in an open circular (OC) conformation, whereby nicking of the SC loop relaxes the DNA into an untwisted loop. One of the most common means of analyzing plasmids electrophoretically is in agarose, whose structure is known to consist of a random, three-dimensional network of long, straight, connected fibers, each made of 10 to 30 double helices (Arnott, S. et al. *J. Mol. Biol* 90:269 (1974); Waki, S. et al *Biopolymer* 21:1909 (1982)). At electric fields above a critical value, trapping of both the SC and OC forms of plasmid DNA has been observed. Two models are commonly used to explain this trapping—the impalement model and the lobster trap model (Akerman, B. et al. *Electrophoresis* 23:2549 (2002)). The impalement model proposes that circular DNA is trapped by becoming caught or impaled upon the free end of a fiber in such a network. In contrast, the lobster trap model posits that the DNA is caught in constricted 'dead-ends' in the sieving matrix.

Akerman (Akerman, B. *Biophys J* 74:3140 (1998)) used an elegant method based on linear dichroism (LD) to study the behaviour of SC and OC DNA in polyacrylamide (PA) and agarose gels under fields of 7.5 to 22.5 V/cm in TBE buffer. Although the supercoiled (SC DNA or scDNA) was not trapped in the agarose gel, in PA the SC DNA showed a "rapidly fading smear" that extended 3-4 mm from the loading well, whereas the OC DNA was trapped immediately. The SC smear was attributed to less efficient trapping of the SC DNA as compared to the OC DNA. Akerman proposed that the circular DNA was trapped by impalement upon protruding fibres within the PA gel, with the OC DNA forming an extended, open loop and the SC DNA forming an extended, twisted loop (Akerman, B. *Biophys J* 74:3140 (1998)). Akerman estimated a characteristic dangling fibre length of between 8.7 and 33 nm for PA.

LD measurements of the time constants of DNA orientation under an electric field, was used this as an indication of the degree of trapping, finding the rate of DNA being trapped was proportional to $E^{-n}$, where n was approximately 2. Transport effects were expected to give a dependence of $E^{-1}$ and the additional contribution of $E^{-1}$ was attributed to having more trapping sites available at higher fields (shorter gel fibres will be able to trap at higher fields). The exponent of this additional contribution was expected to vary depending on the distribution in lengths of dangling fibres. To explain the lower trapping rate of the SC DNA, Akerman suggested that the supercoiling of the DNA reduces the size of the holes in the DNA coil, lowering the probability of penetration by a gel fibre. In addition, the SC DNA presents a smaller cross-sectional area available for impalement. Although that work was limited in the range of SC DNA studied (two sizes, 2926 and 5386 bp), Akerman found that the larger SC DNA was immobilized faster than the smaller. To explain the absence of trapping within agarose, Akerman suggested (and supported with literature values) that the holes in the supercoiled structure were too small to be penetrated by the agarose gel fibres (diameter of 3-9 nm) but not by the fibres of the PA (~0.1 nm in diameter).

Although the relationship between the size of trapped linear DNA and the electric field (E) is well known, and underlies such techniques as pulsed field gel electrophoreses, this trapping relationship for circular DNA is not nearly as well understood. As described above, considerable progress has been made in understanding the behaviour of OC and SC DNA, but in some cases this work has been complicated by the use of imaging techniques that inadvertently nick the fragile SC DNA, thereby converting it to OC DNA

SUMMARY OF THE INVENTION

The present art has suffered from a method to isolate a population of scDNA of particular designed length within a microfluidic device. Further, the art has suffered from the inability to isolate or enrich a sample for mitochondrial scDNA.

The present invention provides for a method for isolation of supercoiled nucleic acid of interest contained within a fluid sample containing at least one other contaminating supercoiled nucleic acid of size greater than the supercoiled nucleic acid of interest comprising introducing said fluid sample into a microfluidic capillary containing a trapping matrix at a first position, application of an electric field to the fluid sample such that supercoiled nucleic acid is encouraged to move within said microfluidic capillary containing a trapping matrix to a second position, distal to said first position;

wherein the electric field applied is chosen so as to be greater than the critical electric field for said at least one contaminating nucleic acid, and less than the critical electric field for said supercoiled nucleic acid of interest;

wherein the critical electric field is the minimum electric field required to trap scDNA molecule of a given size; and wherein the electric field is applied for a period of time sufficient to isolate the supercoiled nucleic acid of interest.

In another aspect, the present invention provides for a method for isolation of supercoiled nucleic acid of interest contained within a fluid sample containing at least one other contaminating supercoiled nucleic acid of size less than the supercoiled nucleic acid of interest comprising introducing said fluid sample into a microfluidic capillary containing a trapping matrix at a first position, application of an electric field to the fluid sample such that supercoiled nucleic acid is encouraged to move within said microfluidic capillary containing a trapping matrix to a second position, distal to said first position;

wherein the electric field applied is chosen so as to be less than the critical electric field for said at least one contaminating nucleic acid, and greater than the critical electric field for said supercoiled nucleic acid of interest;

wherein the critical electric field is the minimum electric field required to trap scDNA of a given size; and wherein the electric field is applied for a period of time sufficient to isolate the supercoiled nucleic acid of interest.

In another aspect the present invention provides for a method for isolation of supercoiled nucleic acid of interest contained within a fluid sample containing at least one other contaminating supercoiled nucleic acid of size less than the supercoiled nucleic acid of interest and at least one other contaminating supercoiled nucleic acid of size greater than the supercoiled nucleic acid of interest comprising introducing said fluid sample into a microfluidic capillary containing a trapping matrix at a first position, application of a first electric field to the fluid sample such that supercoiled nucleic acid is encouraged to move within said microfluidic capillary containing a trapping matrix to a second position, distal to said first position;

application of a second electric field to the fluid sample such that supercoiled nucleic acid is encouraged to move within said microfluidic capillary containing a trapping matrix to a third position, distal to both said first position and second position;

wherein the first electric field applied is chosen so as to be less than the critical electric field for said at least one contaminating nucleic acid of size less than the supercoiled nucleic acid of interest, and greater than the critical electric field for said supercoiled nucleic acid of interest;

wherein the first electric field is applied for a period of time sufficient to isolate the at least one contaminating nucleic acid of size less than supercoiled nucleic acid of interest;

wherein the second electric field applied is chosen so as to be greater than the critical electric field for said at least one contaminating nucleic acid of size greater than the supercoiled nucleic acid of interest, and less than the critical electric field for said supercoiled nucleic acid of interest;

wherein the critical electric field is the minimum electric field required to trap scDNA of a given size; and wherein the electric field is applied for a period of time sufficient to isolate the supercoiled nucleic acid of interest.

In another aspect, the present invention provides for a method for isolation of supercoiled nucleic acid of interest contained within a fluid sample containing at least one other contaminating supercoiled nucleic acid of size less than the supercoiled nucleic acid of interest and at least one other contaminating supercoiled nucleic acid of size greater than the supercoiled nucleic acid of interest comprising introducing said fluid sample into a microfluidic capillary containing a trapping matrix at a first position, application of a first electric field to the fluid sample such that supercoiled nucleic acid is encouraged to move within said microfluidic capillary containing a trapping matrix to a second position, distal to said first position;

application of a second electric field to the fluid sample such that supercoiled nucleic acid is encouraged to move within said microfluidic capillary containing a trapping matrix to a third position, distal to said second position;

wherein the first electric field applied is chosen so as to be greater than the critical electric field for said at least one contaminating nucleic acid of size greater than the supercoiled nucleic acid of interest, and less than the critical electric field for said supercoiled nucleic acid of interest;

wherein the first electric field is applied for a period of time sufficient to isolate the at least one contaminating nucleic acid of size greater than supercoiled nucleic acid of interest;

wherein the second electric field applied is chosen so as to be less than the critical electric field for said at least one contaminating nucleic acid of size less than the supercoiled nucleic acid of interest, and greater than the critical electric field for said supercoiled nucleic acid of interest;

wherein the critical electric field is the minimum electric field required to trap scDNA of a given size; and wherein the first electric field is applied for a period of time sufficient to isolate the supercoiled nucleic acid of interest.

In a preferred embodiment, the fluid sample results from the lysis of a non-eukaryotic or eukaryotic cell. In a still preferred embodiment, the lysis occurs within the same microfluidic device as the microfluidic channel containing a trapping matrix. In one embodiment the supercoiled nucleic acid of interest is a plasmid. In alternate embodiment, the supercoiled nucleic acid of interest is mtDNA.

The present invention contemplates the use of particular electric fields in combination with a trapping matrix, such that a scDNA of particular size is immobilized, or trapped, within the trapping matrix; this is described as the critical electric field ($E_c$ or $E_{crit}$). As shown in FIG. 8 there exist particular critical electric fields for a variety of scDNA sizes. One skilled in the art will recognize that the particular critical electric field for a given scDNA is a function of the trapping matrix, as well as the concentration of the polymer forming the trapping matrix. One skilled in the art will be able to determine the critical electric field for a particular scDNA using the teachings and methods disclosed herein.

In another aspect, the present invention provides for a method to isolate supercoiled nucleic acid from chromosomal DNA in a cell of interest comprising
  introducing at least one cell into an input well on a microfluidic device in fluid communication with a microfluidic channel
  lysing said cell within said input well creating a lysis product
  electrophoretically transferring said lysis product from the input well to the microfluidic channel
  applying a electric field to the lysis product such that supercoiled nucleic acid is encouraged to move within said microfluidic capillary containing a trapping matrix;
  wherein the electric field applied is chosen so as to be less than the critical electric field for the supercoiled nucleic acid;
  wherein the critical electric field is the minimum electric field required to trap scDNA of a given size; and
  wherein the electric field is applied for a period of time sufficient to isolate the supercoiled nucleic acid from the chromosomal DNA.

In one embodiment the supercoiled nucleic acid is a plasmid. In an alternative embodiment the supercoiled nucleic acid is mitochondrial DNA.

In another aspect, the present invention provides for a method to immobilize supercoiled nucleic acid of interest contained within a fluid sample comprising
  introducing said fluid sample into a microfluidic capillary containing a trapping matrix,
  applying an electric field to the fluid sample such that the electric field is greater than the critical electric field for said supercoiled nucleic acid of interest;
  wherein the critical electric field is the minimum electric field required to trap a scDNA molecule a given size within the trapping matrix; and
  wherein the electric field is applied for a period of time sufficient to isolate the supercoiled nucleic acid of interest.

In one embodiment, the supercoiled nucleic acid is transported through the trapping matrix to a pre-determined point, at which time the electric field applicable to the supercoiled nucleic acid is raised to a value greater than the critical electric field for the supercoiled nucleic acid. It is contemplated that such immobilization of supercoiled nucleic acid, combined with other means of fluid transport within a microfluidic device, will be useful for the washing, or changing of the ion, buffer, protein or other molecules present within, or surrounding the supercoiled nucleic acid.

In another aspect, the present invention provides for a method to isolate supercoiled nucleic acid from chromosomal DNA of size greater than the supercoiled nucleic acid and contaminating non-supercoiled nucleic acids in cells comprising
  introducing at least the cells into a first input position on a microfluidic device containing at least one input position and at least one output position in fluid communication through at least one microfluidic channel containing a trapping matrix;
  lysing said cells within said input well creating a lysis product
  wherein the electric field is applied for a period of time sufficient to transfer at least the supercoiled nucleic acid from the input position to the output position using at least one microfluidic channel containing a trapping matrix.

In one embodiment, the trapping matrix is 0.6% agarose and 1×TTE; and the electric field is between 10 V/cm and 100 V/cm. In a preferred embodiment the trapping matrix is 0.6% agarose and 1×TTE; and the electric field is between 20 and 40 V/cm and in an even more preferred embodiment the electric field is 30 V/cm. In another embodiment said input position and output position are wells within the microfluidic device.

In another aspect the present invention provides for a method to isolate supercoiled nucleic acid from chromosomal DNA of size greater than the supercoiled nucleic acid and contaminating non-supercoiled nucleic acids in cells comprising
  introducing at least the cells into an input well on a microfluidic device containing at least one input well, at least one output well and at least one waste well in fluid communication through at least one microfluidic channel containing a trapping matrix;
  lysing said cells within said input well creating a lysis product
  applying a first electric field such that at least the supercoiled nucleic acid is electrophoretically transferred from the at least one input well to the at least one microfluidic channel;
  applying a second electric field to the supercoiled nucleic acid in the microfluidic channel;
  applying a third electric field to the supercoiled nucleic acid in the microfluidic channel;
  wherein the second electric field applied is chosen so as to be greater than the critical electric field for the supercoiled nucleic acid;
  wherein the critical electric field is the minimum electric field required to trap a supercoiled nucleic acid molecule of a given size;
  wherein the second electric field is applied for a period of time such that substantially all contaminating non-supercoiled nucleic acids are transferred to the at least one waste well;
  wherein the third electric field applied is chosen so as to be less than the critical electric field for the supercoiled nucleic acid; and
  wherein the third electric field is applied for a period of time sufficient to transfer at least the supercoiled nucleic acid from at least one microfluidic channel to the at least one output well using at least one microfluidic channel.

The accompanying description illustrates preferred embodiments of the present invention and serves to explain the principles of the present invention

DETAILED DESCRIPTION OF THE PRESENT INVENTION

Figure 1:
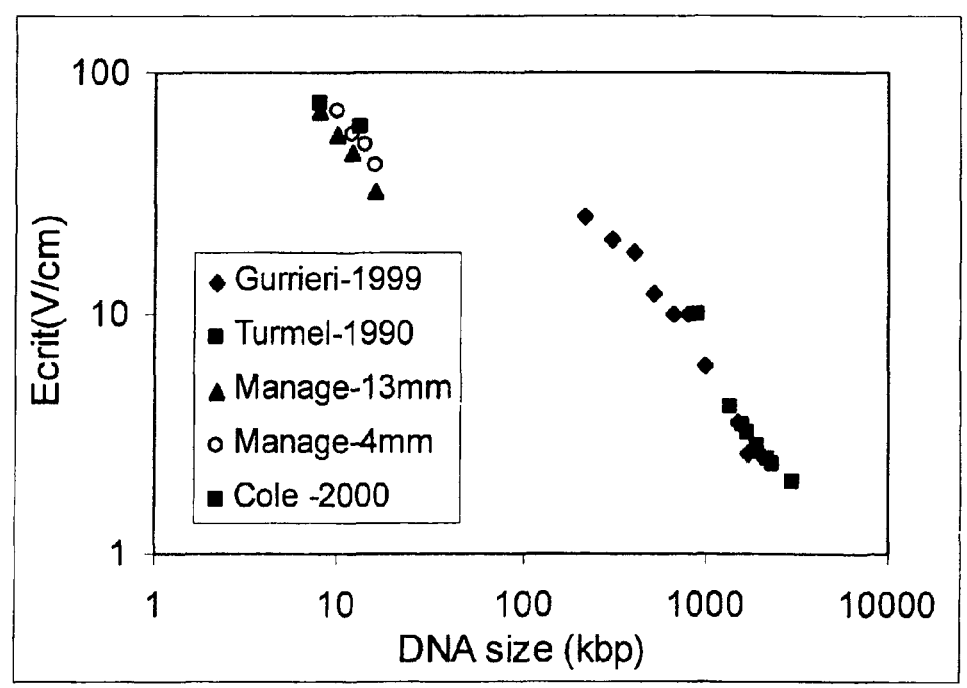
FIG. 1 shows a log-log plot of critical electric fields vs. the size of DNA comparison demonstrating the relationship between $E_{crit}$ and molecule size for different species of DNA.

As used herein, the term "clinical sample" means a fluid or tissue originating from a human. The sample may either be unmodified, or alternatively the sample may be processed before introduction into the devices of the present invention. Processing is contemplate to include, but not be limited to, pH alteration, ion removal, ion addition, cell separation, cell purification, cell removal, protein removal or cell lysis, nucleic acid enrichment, nucleic acid isolation, nucleic acid separation and nucleic acid purification; all of which give rise to a sample for analysis which would enrich the sample for the nucleic acid of interest, if present.

As used herein, "microfluidic devices", sometimes termed "lab on a chip", "microfluidic chips" "microchips", "chips" or "microsystem platforms" refer to the result of applying microelectronic fabrication technologies to produce a network of wells and channels etched into glass and/or molded into polymers that are bonded to glass or silicon chips. A wide range of chip materials are known in the art, with a number of materials possible, so long as generally nonconductive. Within these wells and microchannels, cells and reagents can be manipulated by a variety of methods including gravity feed, applying electric or magnetic fields and results detected by, for example, image analysis or optical means. Microfluidic chips provide for PCR reactions and analysis of PCR products (Footz, T. S. et al. *Electrophoresis* 22:3868 (2001); Obeid, P. J. et al. *Anal Chem* 75:288 (2003); Backhouse C. J. et al. *Electrophoresis* 24:1777 (2003)). They enable high resolution separations through polymer-filled microchannels using capillary electrophoresis of e.g. multiple PCR products, and can exhibit a high level of integration by combining multiple functions on a single chip, for example cell sorting and RT-PCR reactions for gene expression or genomic profiles of a given cell or population of cells (Backhouse, C. J. et al. *Proceedings of the International Conference on MEMS, NANO and Smart Systems* 377 (2003)). Within a microfluidic device, sample processing can be implemented and cells can be separated by a variety of means, including dielectrophoresis, and processed in a variety of ways, including analysis of HAS gene expression as shown here. In the future, microsystem platforms incorporating microfluidics chip-based sample processing and analysis may replace more conventional methodologies for applications such as genotyping.

As used herein the term "isolated" is intended to mean that the nucleic acid of interest exists in a physical milieu distinct from that in which it was initially introduced into the device of the present invention and/or has been completely or partially separated or purified from other nucleic acid molecules, proteins, carbohydrates or lipids.

As used herein the terms "selective" and "selectively" refer to the ability to isolate a particular species of DNA molecule, on the basis of molecular size (e.g., host cell chromosomal DNA, exogenous plasmid DNA, mitochondrial DNA), from a combination which includes or is a mixture of species of DNA molecules, such as a host cell lysate and other host cell components. The selective isolation of a particular species is accomplished through selective application of an electric field, or repeated application of different electric fields, such that the scDNA of interest are selectively separated, or isolated, from other molecules.

The present invention provides for the separation of supercoiled DNA of sizes ranging up to 20-25 kilobases, from the larger scDNA, megabase DNA, linear DNA, or OC DNA; by way of non-limiting example, chromosomal DNA; as well as separation from proteins or cellular debris and components normally associated with cellular lysis. As disclosed herein, the novel discovery of the electrophoretic behaviours of a complex mixture of supercoiled DNA molecules in agarose-filled microchannels on a microfluidic device may be exploited to provide for a novel method for supercoiled nucleic acid enrichment, separation or purification. A novel finding is that there are distinctly different modes of behaviour for supercoiled DNA, depending on whether the applied electric field in the electrophoresis was at, above, or below, a critical field value. Whether the scDNA was of small enough size that no trapping by the agarose was ever seen (by way of non limiting example, 4 kb), or large enough that trapping by the agarose occurred, the mobility vs. field (FIG. 7) shows a similar behaviour (for all plasmid sizes) that was unaffected by nearness to the critical field value. However, as the critical field is reached (FIG. 9), the attenuation becomes severe enough that the peaks disappear even though there is no apparent effect on the mobility. In the prior art impalement model there is a distribution of trapping times that arise from scDNA impalement upon a distribution of fibre lengths, thereby producing (at all fields) an effect upon the mobility and a strong dependence of trapping times upon the field strength. Contrary to this conventional notion and as disclosed herein, when the DNA is trapped it remains so until the fields are reduced—there is no evidence of a distribution of trapping times that, in the conventional impalement model, gives rise to the strong field dependence. Since there does not appear to be a field dependence of the detrapping times, it is hypothesized, but not necessary to practise the present invention, that the strong field-dependence of trapping effects is due to a field-dependence of the capture of SC DNA—a new phenomenon.

Figure 7:
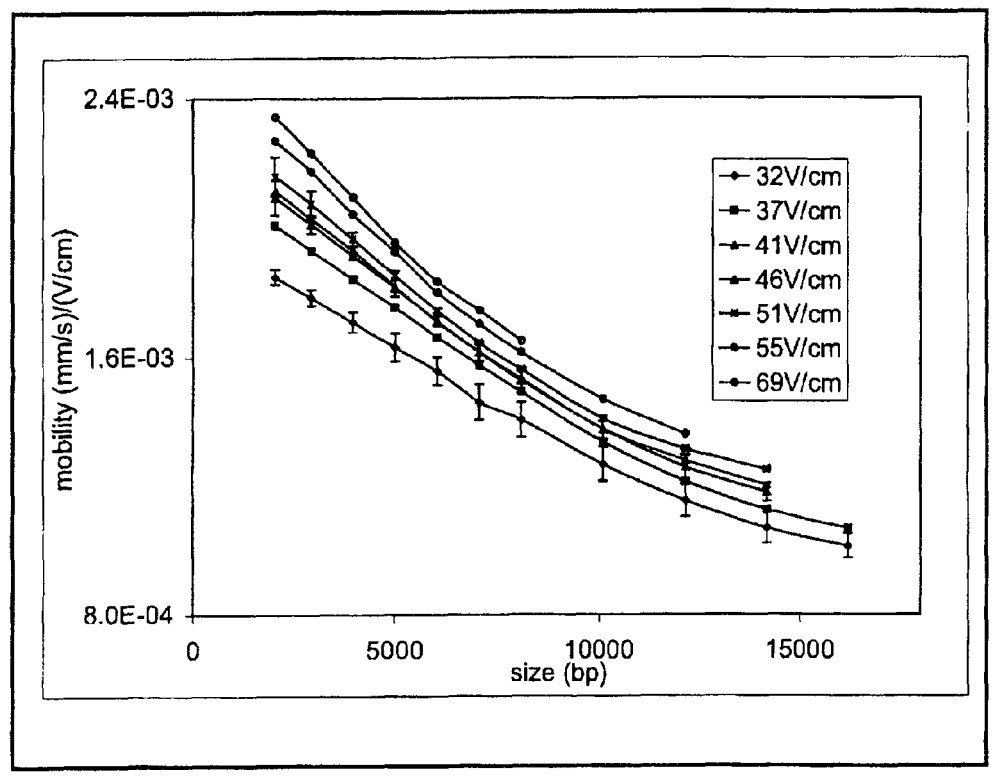
FIG. 7 shows the mobilities calculated from the separation of the SC ladder at various electric fields, with detection at 4 mm, though longer SC DNA species were not detectable at higher fields due to compete attenuation of peaks.
Figure 9:
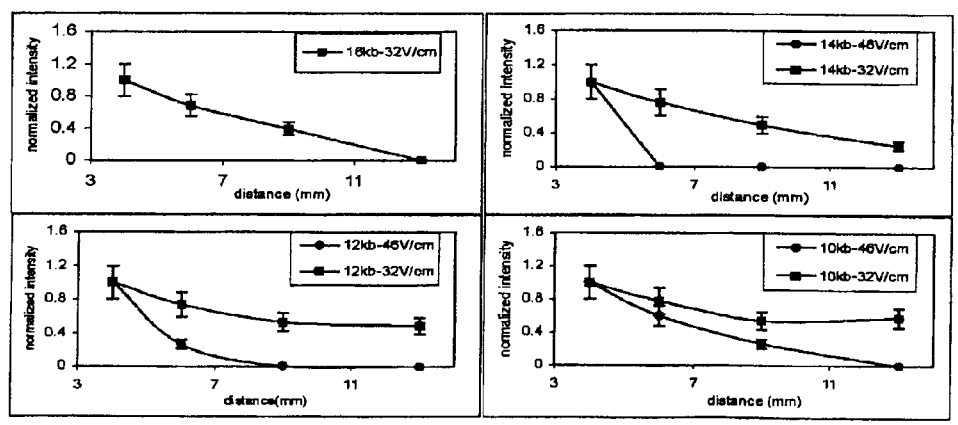
FIG. 9 shows the normalized peak intensities versus distance for one or two applied fields, for various sizes of SC DNA, with separation in 0.6% agarose in 1×TTE buffer.

As shown in FIG. 9, the onset of trapping of scDNA by agarose, is so sudden that it is difficult to detect the degree of trapping since the peaks are either present with little attenuation, or entirely absent. There is not, contrary to the prior art, a distribution of fibre lengths within an agarose medium containing scDNA, with shorter fibre lengths trapping scDNA for shorter periods of time, thereby reducing mobility of scDNA. Rather there is a critical field at which all mobility ceases, while below this critical field, mobility increases with increased electric field (FIG. 7). More specifically, all fibres can trap scDNA for a period of time that is long, compared to the separation time within the microfluidic channel. As demonstrated herein, the observed effects are not a result of overloading of a limited number of traps.

It is therefore contemplated as part of the present invention to exploit these novel findings in order to separate scDNA of desired size from other molecules, in particular separation of scDNA of desired size from proteins, carbohydrates, lipids and other cellular debris associated with the cell lysis required for access to scDNA; as well as separation of scDNA of desired size from scDNA of undesired size; by way of non-limiting example megabase DNA such as chromosomal nucleic acids.

It is further contemplated that the separation occurs on a microfluidic device comprising at least one microfluidic channel with at least one input well in fluidic communication therewith, capable of receiving a sample containing scDNA; the microfluidic channel containing a matrix with the ability to provide trapping of scDNA at critical electric fields in combination with a suitable buffer (a "trapping matrix"). As disclosed herein, this matrix may be agarose. One skilled in the art would be able to provide alternative matrixes, for example including but not limited to polyacrylamide; as well as buffers appropriate for application of electorphoretic forces upon the scDNA, including but not limited to TTE buffer or standard sodium citrate buffer.

It is contemplated by the present invention that the application of specific electric fields to a sample containing scDNA, such that the electric field is above the critical electric field ($E_{crit}$ or $E_c$), for a certain population of scDNA, while being below the critical electric field for a second population of scDNA, will result in the movement of the second population of scDNA away from the first population of scDNA. By successive application of electric fields, such that the electric field is above the critical electric field for certain populations while below the critical electric field for other populations, it is possible to sequentially move and separate a population of scDNA from others. It is contemplated that a population of scDNA is characterized by its size, as measured in base pairs; although one skilled in the art will realize that the amount of supercoiling within a DNA population will also result in variation of critical electric fields and the ability to selectively move and separate a population of DNA based upon supercoiling. One skilled in the art will recognize that supercoiling variation may arise due to the base pair composition of the DNA, from intercalation of imaging molecules such as ethidium bromide or sytox orange, or from enzyme interaction with the DNA such as site specific nicking by a restriction endonuclease. Intentional modification of supercoiling of DNA so as to modify its critical electric field in a particular matrix is contemplated by the present invention.

The present invention contemplates a microfluidic device comprising at least one input well in fluid communication with at least one microchannel with at least one of said at least one microchannels containing a trapping matrix. Such a device may be used to separate at least one population of scDNA from other scDNA or contaminating molecules or macromolecules, for further processing by a microfluidic device. In a preferred embodiment the scDNA of interest is directed from sample waste reservoirs 1102 or buffer waste reservoirs 1204 for further processing. In another embodiment, sample waste reservoirs 1102 or buffer waste reservoirs 1204 are used as a PCR chamber for further processing of the scDNA, said PCR chamber contemplated to be in fluid communication with a microchannel for capillary electrophoresis as is known in the art (not shown).

Within a microfluidic device, following the separation or isolation of a population of scDNA of interest, the scDNA may be used for further processing, such processing and methods for moving the scDNA within a microfluidic device known in the art. By way of non-limiting example, the scDNA may be used within a polymerase chain reaction or hybridized with a probe to detect the presence of a nucleic acid base pair sequence. Various methods of fluid transfer are known in the art and contemplated by the present invention, for example a series of adjacent valves activated in sequence creating a microfluidic equivalent of peristaltic pumping are known by those skilled in the art. See, by way of non-limiting example, US 20040209354 by Mathies. Further, the details on integrated PCR-CE system are described elsewhere (Kaigala, G. V. et al. *Electrophoresis* 27:3753 (2006)).

It is contemplated by the present invention that the isolation/separation methods disclosed herein can be applied to a complex sample of scDNA, in which contaminating molecules are present, or to a sample comprising a multiplicity of cells. In a preferred embodiment the sample comprising a multiplicity of cells is placed directly in a microfluidic device, for example in an input well in fluidic communication with at least one microfluidic channel with a trapping matrix. Advantageously, the cells may be lysed and the scDNA of interest separated within the microfluidic device, which significantly increases the yield of scDNA from a samples comprising intact cells.

It is also contemplated that the present invention may be used to isolate plasmid DNA from chromosomal DNA in a sample containing a multiplicity of cells. This may be performed on either eukaryotic or non-eukaryotic cells. As well, it is contemplated that the present invention may be advantageously used to isolate mitochondrial DNA (mtDNA) from a sample containing a multiplicity of eukaryotic cells. mtDNA molecules are of various sizes, though generally known to be approximately 16.5 kb closed circular double-stranded molecules (Shadel, et al *Annu Rev Biochem* 66:409 (1997)) and are observed in amounts varying from hundreds to tens of thousands of copies per cell. In this way, they are very similar to plasmids, and it is therefore contemplated that the methods disclosed herein with respect to plasmids within eukaryotic cells may be applied by one skilled in the art, for mitochondrial DNA preparations.

The present invention provides for a rapid plasmid miniprep method for eukaryotic or non-eukaryotic cells, such as cultured human fibroblasts containing a plasmid that makes use of a modification of standard lab-on-a-chip methods. As disclosed herein, predictable trapping of plasmid DNA (pDNA) with fields on the order of 100 V/cm, while the trapping of OC DNA and chDNA are known to occur at fields on the order of 10 and 1 V/cm, respectively. This provides an electrophoretic window between 10 and 100 V/cm, depending on plasmid size, within which pDNA can be mobilized while leaving the OC and chDNA to be trapped within the sieving matrix. An essential component of such a separation is therefore the absence of shearing of the chDNA, which can only be achieved by avoiding any manipulation of the chDNA after cell lysis. It is known in the art that the standard protocols used for DNA purification results in shearing of megabase-sized DNA, thereby producing DNA fragments significantly smaller than intact chDNA. Together with the differential electrophoretic behaviour of the supercoiled plasmid DNA, the present invention provides for a microfluidic chip-based mini-prep that is simple, fast and efficient that will greatly assist the implementation of applications requiring plasmid DNA analysis and further manipulation.

In order to ensure that the chDNA is kept intact, it is critical to lyse the cells on-chip. It is well-known that the standard protocols used for DNA purification result in DNA shearing, thereby producing the DNA fragments far smaller than chDNA. Therefore, in order to have intact chDNA, the cells on the microfluidic chip were lysed by osmotic shock, thereby releasing the DNA without creating hydrodynamic shearing effects.

Figure 11:
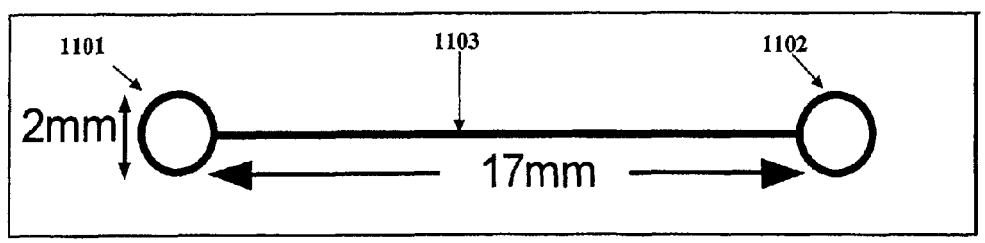
FIG. 11 shows a schematic of the two well glass microchip used herein consisting of a sample reservoir (SR) 1101 and a sample waste reservoir (SW) 1102 linked by a 45 μm deep microchannel.

Human cell lines with a commercial plasmid added were utilized to demonstrate the utility of the present invention. Care was taken to ensure that the quantities of DNA of each type were representative of that from a plasmid-bearing cell lysate. After cell lysis, pDNA was added for positive controls, and not added for negative controls. Using the microfluidic chip as shown in FIG. 11, an electric field was applied to move the pDNA from the sample reservoir through the agarose-filled channel and into the sample waste reservoir. Once separated, plasmid-specific and chDNA-specific PCR was performed on the contents of the sample waste reservoir to demonstrate that the pDNA moved through agarose whereas the chDNA was trapped.

It is believed that the simple, fast and efficient separation method of the present invention can greatly assist the implementation of plasmid applications. Cell lysis, separation of plasmids from chDNA, PCR, enzymatic digestion, and separation of PCR products by capillary electrophoresis can be implemented on a single microchip, allowing the whole process to be performed on a time scale of minutes.

This work provides for a method and apparatus for reliable separation of scDNA, such as pDNA or mtDNA, from megabase-scale chromosomes and other contaminating macromolecules such as proteins, lipids and carbohydrates resulting from cell lysates. On-chip lysis of human cells by osmotic shock releases the chDNA without creating hydrodynamic shearing effects. Once separated, plasmid-specific and chDNA-specific PCR was performed on the contents of the sample waste reservoir to prove that the pDNA moved through agarose whereas the chDNA was trapped. Although it was convenient for to use human cells for the present work, this method could readily be extended to bacterial and other cell types, though this would likely require adaptations to the cell lysis procedure, such adaptation is known in the art.

Materials and Methods

Unless otherwise stated, similar conditions were used for experiments relating to supercoiled DNA separation mechanics, as were used for demonstration of plasmid separation.

Reagents

For the initial channel coating, 40% acrylamide monomer, 92% 3-(Trimethoxysilyl) propyl acrylate, glacial acetic acid, N,N,N',N'-Tetramethylethylenediamine (TEMED), and potassium persulfate were obtained from Sigma-Aldrich (St. Louis, Mo., USA). Tris Taps EDTA (TTE) buffer was prepared from DTA (Sigma, USA), TAPOS (Sigma, USA) and Tris (Fisher Scientific, Canada) with the 10× stock solution being 500 mM Tris-base, 500 mM TAPS and 10 mM Sodium-EDTA. The 0.6% (w/v) agarose in 1×TTE is made from agarose-III (PFGE grade; Amresco, USA) and kept at 65° C. until the chip was filled, as described below. PCR reagents (polymerases and buffers) were purchased from Invitrogen (Burlington, ON, Canada).). A working solution of 1 µM Sytox Orange (SO) was made by dissolving the stock solution (5 mM in DMSO; Invitrogen, USA) in water. The SC DNA ladder (with approximate sizes 16.2 kb, 14.2 kb, 12.1 kb, 10.1 kb, 8.1 kb, 7.0 kb, 6.0 kb, 5.0 kb, 4.0 kb, 3.0 kb, 2.0 kb bases), has a total concentration of 0.25 µg/µl in equal mass quantities per band (i.e. approximately 0.024 µg/µl for each band). This ladder was purchased from Invitrogen and was derived from a strain harbouring 11 plasmids. No extra bands, resulting from nicking or damage to the SC DNA of the ladder, were observed.

Biological Samples: GM01 Fibroblast Cells

GM01 fibroblasts were grown to confluence in 75 cm$^2$ culture flasks with 0.2 µm vent cups (Corning Inc., Corning, N.Y., USA). In a humidified atmosphere of 5% $CO_2$-95% air in Eagle's Minimum Essential Medium (µ-MEM, Invitrogen, Burlington, ON, Canada) containing 10% (v/v) fetal bovine serum, supplemented with uridine (50 mg/l) and pyruvate (100 mg/l). Cells were harvested using 3 ml of 0.125% (w/v) trypsin in phosphate-buffered saline (PBS; Invitrogen). Trypsinization was stopped by the addition of 12 ml µ-MEM/10% FBS and cells were washed and resuspended in PBS. Prior to each experiment, the cells were counted using a hemocytometer (Hausser Scientific Partnership, Horsham, Pa., USA).

DNA Preparation

The pCOX15 plasmid (6.1 kb) used in this study contains a 1.7 kb HindIII-BamHI fragment containing the yeast COX15 gene (Glerum et al, *J Biol Chem* 272:19088 (1997)) cloned into YCplac111. It was expressed in *E. coli* and purified by standard techniques. Human genomic DNA (gDNA) used in the positive controls was prepared from lymphocytes using standard methods (Gustincich S, et al. *BioTechniques* 11:298 (1991)). The procedure for purification of human gDNA is summarized as follows.

The medium from 5 confluent plates (100 mm Tissue Culture Dishes, Corning Inc, Corning, N.Y., USA), was suctioned off, and the cells washed with 1 ml PBS. Cells were harvested using rubber spatula. The cells were then sedimented (3000 xg for 5 min at 4° C., supernatant was discarded) and resuspended in 0.9 ml of PBS, An equal volume of 12% dodecyltrimethylamonium bromide (DTAB, Sigma) solution (12% DTAB, 2.25M $NaCl_2$, 150 mM Tris-HCl, pH 8.6, 75 mM EDTA) was added to the cell suspension, gently mixed and incubated for 5 min at 68° C. After addition of two volumes of chloroform, sample was vigorously mixed and centrifuged for 2 min at 10,000 xg. The aqueous layer was transferred to a new tube containing 2 volumes of 0.5% hexadecyltrimethylammonium bromide (CTAB, Sigma) solution (0.5% CTAB, 0.04M NaCl) After mixing and spinning, the supernatant was discarded and the DNA-CTAB pellet was resuspended in 0.3 ml of a 1.2 M $NaCl_2$ solution. To precipitate the DNA, 0.750 ml of 100% EtOH was added. After spinning for 2 min at 14,00 xg, the DNA pellet was washed twice with 70% EtOH, centrifuged for 2 min at 14,000 xg, vacuum-dried for 10 min (SpeedVac Plus SC110 A, Savant), and resuspended in 50-200 µl sterile TE buffer (10 mM Tris-HCl, 0.1 mM EDTA, pH 7.6) or miliQ water. The concentration of purified DNA was determined in a UV-1601 PC spectrophotometer (Shimadzu Corp., Japan). This extensive preparation process was required only for the production of the genomic DNA (gDNA) used for controls.

Microchip Analysis: Plasmid Separation

Figure 12:
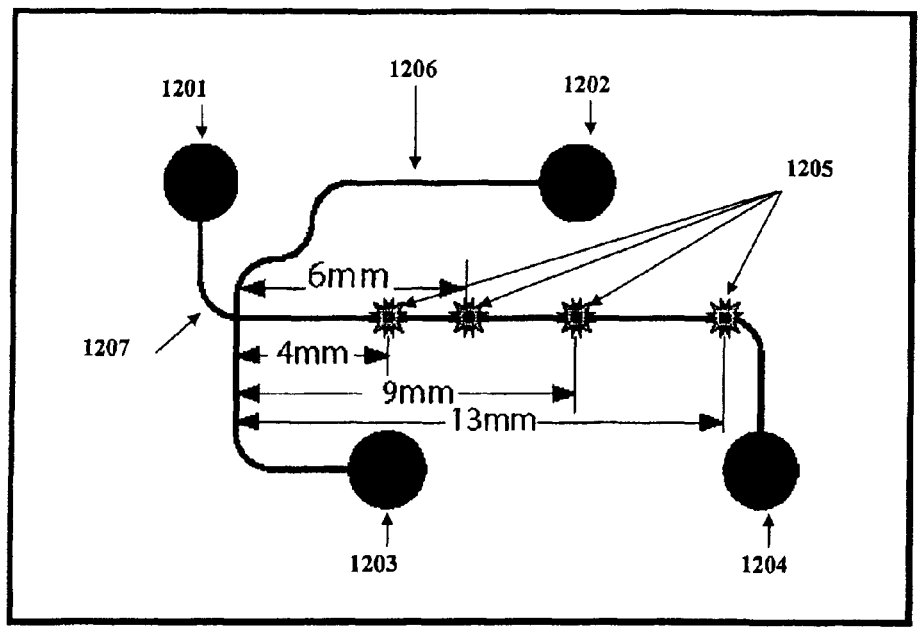
FIG. 12 shows a schematic of a 4 reservoir glass microchip used herein consisting of a buffer reservoir (BR) 1201, sample waste reservoir (SW) 1202, sample reservoir (SR) 1203, buffer waste reservoir (BW) 1204 and detection locations 1205.

The glass microchips of the present invention have dimensions of 2.4 cm×1.6 cm. FIG. 11 shows a simplified representation of the glass microchip, with 2 reservoirs 1101 and 1102 linked by a microchannel 1103 that has an approximately semi-circular cross section. The reservoirs 1101 and 1102 are 2 mm in diameter and 1.1 mm deep, each holding ca. 3 µL. The glass microchips were fabricated by standard glass etching and fusion bonding processes Microchip Analysis: Supercoiled DNA Separation Mechanics The glass microchips were fabricated by standard glass etching and fusion bonding processes with dimensions of 2.4 cm×1.6 cm and microchannels 1206 and 1207 that are 100 µm wide and 45 µm deep. FIG. 12 shows the schematic of the microfluidic chip, which has an effective separation channel 1207 (from the intersection to the curve) of 13 mm Reservoirs 1201, 1202, 1203 and 1204 are 2 mm in diameter and capable of holding approximately 3 µL of liquid.

Microfluidic Channel Coating

The glass microchips were rejuvenated by filling the channels with concentrated $H_2SO_4$ through capillary forces and subsequent heating on a hot plate at 350° C. for 15 min. Following cooling, the chip was rinsed with distilled water, immersed in 1 N NaOH for 10 min, and then washed with water and dried by flowing pressurized nitrogen through the channels. In order to coat the channels, 5.75 mM acetic acid (pH~3.5) containing 0.4% 3 (Trimethoxysilyl)propyl acrylate was injected into the channels 1206, 1207 and 1103 respectively and incubated for 1 hr in order to functionalize the glass surface. The channels were then rinsed with water and dried, in preparation for the permanent linear polyacrylamide coating. The coating precursor solution consisted of 4% (w/v) acrylamide monomer and 0.1% (w/v) potassium persulfate, to which 0.1% (v/v) TEMED was added following a 10 min sonication. The channels were left in the coating solution for 30 min and then thoroughly rinsed with water and dried under a stream of nitrogen (as described above). This procedure passivates the microchannel surface with a thin layer of linear polyacrylamide that ensures adhesion of the agarose to the microchannels.

Chip Loading: Supercoiled DNA Separation Mechanics

Prior to filling the microchannels with agarose (~20 sec), the chip was heated to 40° C. on a preheated metal block. 4 µl of 0.6% warm agarose was placed in the SW well 1202 in order to fill the channels 1206 1207 by capillary forces. The other wells were then filled with 3 µl of agarose solution and the chip was left at room temperature for 20 min to allow the agarose to gel. Solid agarose was then removed from wells 1201 1202 1203 1204 and the chip was loaded with buffers and sample. The ratio of DNA base pairs to SO molecules is 600:1 and the impact on DNA charge, mobility and winding is negligible for the purposes of the present invention.

Chip Loading: Plasmid Separation

In order to stop any contamination of SW well 1102 by the aerosols created during the loading of the cells and plasmid into SR well 1101, SW well 1102 was covered with a cover slip. SR was loaded with 0.7 µl of water, 0.6 mL of 5 mg/µl bovine serum albumin (BSA), 0.3 µl of 1×TTE, 1 µl of GM01 fibroblast cells (1500 cells), and 0.4 µl of 0.25 pg/µl plasmid DNA (1 pg) This is sufficient to effect osmotic lysis of the GM01 fibroblast cells. BSA was added in order to stop the DNA from sticking to the passivated glass surfaces. The cover slip was removed and SW well 1102 was then filled with 2.4 µl of 1×TTE and 0.6 µl of 5 mg/mL BSA. Care was taken to ensure that the quantities of DNA of each type were representative of that from a plasmid-bearing cell lysate. The number of fibroblasts applied is necessarily limited by the ability to carry out an osmotic lysis in the 3 µl volume of SR well 1101. The quantity of pDNA used (1 pg) represents the expected yield from 1500 cells. Given that transfection efficiencies are typically analyzed in terms of percentage of cells that have taken up a plasmid construct, it is not possible to determine the amount of plasmid one might expect to obtain from a known amount of transfected mammalian cells.

Electrophoresis: Supercoiled DNA Separation Mechanics

The electrophoresis and laser-induced fluorescent detection of the SO-labelled DNA was performed with a Microfluidic Toolkit (Micralyne, Edmonton, Canada) with excitation at 532 nm and detection at 570 nm. A field of 43 V/cm was applied between the SR well 1203 and SW well and 1202 for 300 sec, in order to drive the sample along the injection channel 1206. Electrophoretic separations were then performed by applying fields in the range of 32-70 V/cm between the BR well 1201 and BW well 1204. Each such separation would analyse scDNA present in the intersection by moving it to the detection points 1205 located at one of the positions shown in FIG. 12. Subsequent separations were done with 30 sec for each injection. Electropherograms were obtained at distances of 4 mm, 6 mm, 9 mm, and 13 mm in the separation channel. In order to assess intensities of the peaks generated by the SC molecules, the relative intensities of the peaks in the electropherograms were compared. As the electropherogram peaks had not been baseline-resolved, it was not appropriate to compare the area under each peak.

Capillary Electrophoresis (CE): Plasmid Separation

As disclosed herein, it is demonstrated that an electric field of 30 V/cm is insufficient to trap a 7 kb plasmid, but high enough to trap molecules of the size associated with chDNA. Given the projected mobility of a 7 kb plasmid, approximately 0.0015 (mm/s)/(V/cm), the migration of the pCOX15 plasmid to the SW well 1102 was predicted as taking 350 sec, with a channel of 1.7 cm. The CE stage was run for 500 sec to allow for a sufficient amount of pDNA to arrive in the SW well 1102 but not so long that the SW well 1102 and SR well 1101 could dry out. It is contemplated that alternative microfluidic chip designs with shorter channels will allow for shorter electrophoretic processing times, as a 4 mm separation channel would require only a 100 sec run.

Example 1

Demonstration of Super-Coiled Plasmid DNA Trapping

After loading the SR 1203 and performing cell lysis, as explained previously, and after performing CE as explained above, the contents in the SR well 1101 and SW well 1102 were collected into PCR tubes and divided equally into two PCR tubes, allowing for chDNA- and pDNA-specific PCRs to be performed and analyzed.

The PCR reaction mixture to detect the plasmid DNA consisted of 1×PCR buffer, 1 mM MgCl2, 0.1 mM dNTPs, 20 µM of the forward and reverse primers, 2.5 units of Taq DNA polymerase, and template DNA (collected from the chip or from the positive controls). As a positive control, a PCR reaction with 37 ng of purified pDNA was also analyzed as this corresponded to the amount of pDNA loaded onto the chip. The primers were designed to amplify a 1.7 kb fragment of the yeast COX15 gene: forward primer, SEQ ID NO. 1, reverse primer SEQ ID NO. 2. Cycling conditions for the plasmid-specific reactions were as follows: 2 min at 94° C., then 31 cycles of 15 sec at 94° C., 20 sec at 57° C. and 1 min at 68° C., followed by a final extension at 72° C. for 5 min. The thermocycler used was a PTC-200 (MJ Research, Hercules, Calif., USA).

As is standard practice for PCR, the reactions for each pair of primers must be optimized. The above values fall within the conventional ranges for PCR protocols. The PCR mixtures specific for amplification of a fragment from the human nuclear genome (chDNA) were essentially the same as those for the amplification of the plasmid-specific sequences, except that 4 µg of BSA was added to optimize the PCR. Additionally, 3.2 µM of each of the forward and reverse primers were used for amplification of a 345 bp fragment containing exon 2 of the human COX/1 gene: SEQ ID NO. 3, forward primer; and SEQ ID NO. 4, reverse primer. The reactions were cycled for 2 min at 94° C., then 35 cycles of 30 sec at 94° C., 30 sec at 50° C. and 30 sec at 72° C., with a final extension at 72° C. for 10 min. The products amplified by PCR were analyzed by standard means, using electrophoresis in a 1% (w/v) agarose gel and visualization by UV-transillumination of the ethidium bromide-stained gel As disclosed herein, the applied electric field strength dictates the minimum size of the SC DNA that can be trapped during electrophoresis of these molecules through agarose. Indeed, the behaviour of linear DNA under the influence of an electric field has been extensively studied. In FIG. 1, the critical fields ($E_{crit}$—minimum electric field required to trap a DNA molecule of a certain size) are plotted against the size of DNA molecules, as demonstrated in the works of Turmel (Tunnel, C. Et al. *Nucl Acid Res* 18:569 (1990)), Cole (Cole, K. D. et al. *Biomacromol* 21:771 (2000)) and Gurrieri (Gurrieri, S. Et al. *Proc Natl Acad Sci USA* 96:453 (1999)), along with the results for pDNAs with sizes of 16 kb. An inverse relationship between the $E_{crit}$ ($E_c$) and scDNA size is observed. The plotting of these data serves to clearly illustrate a gap between about 10 V/cm and 100 V/cm, within which the SC DNA can move without allowing chDNA to move. Based on these results, it was decided that an electric field of 30 V/cm could be expected to be low enough to allow pDNA to pass through the agarose, while being high enough to trap the much larger chDNA.

Figure 2:
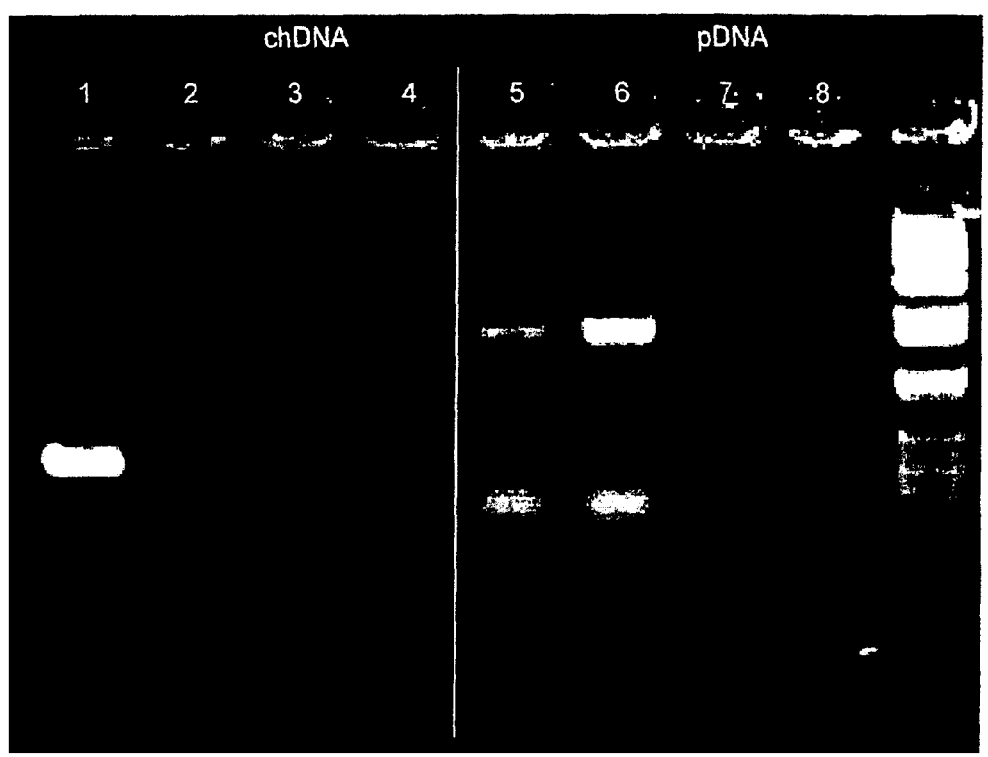
FIG. 2 shows chDNA specific PCR performed on the contents collected from the SR (lane 1 and 2) and pDNA-specific PCR (lane 5 and 6), with lanes 3, 4, 7 and 8 representing internal controls.
Figure 3:
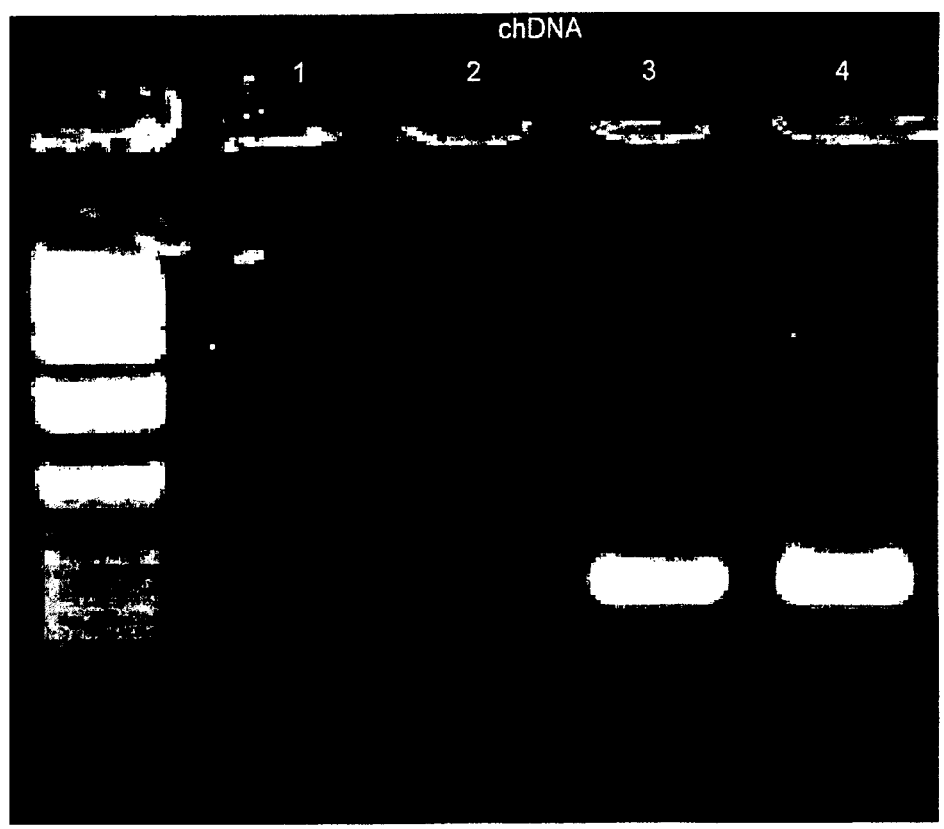
FIG. 3 shows control PCRs for chDNA: negative (water) (lane 1), negative (1×TTE) (lane 2), 1500 cells and 3 μL, 0.6% agarose (lane 3), and 1500 cells (lane 4)
Figure 4:
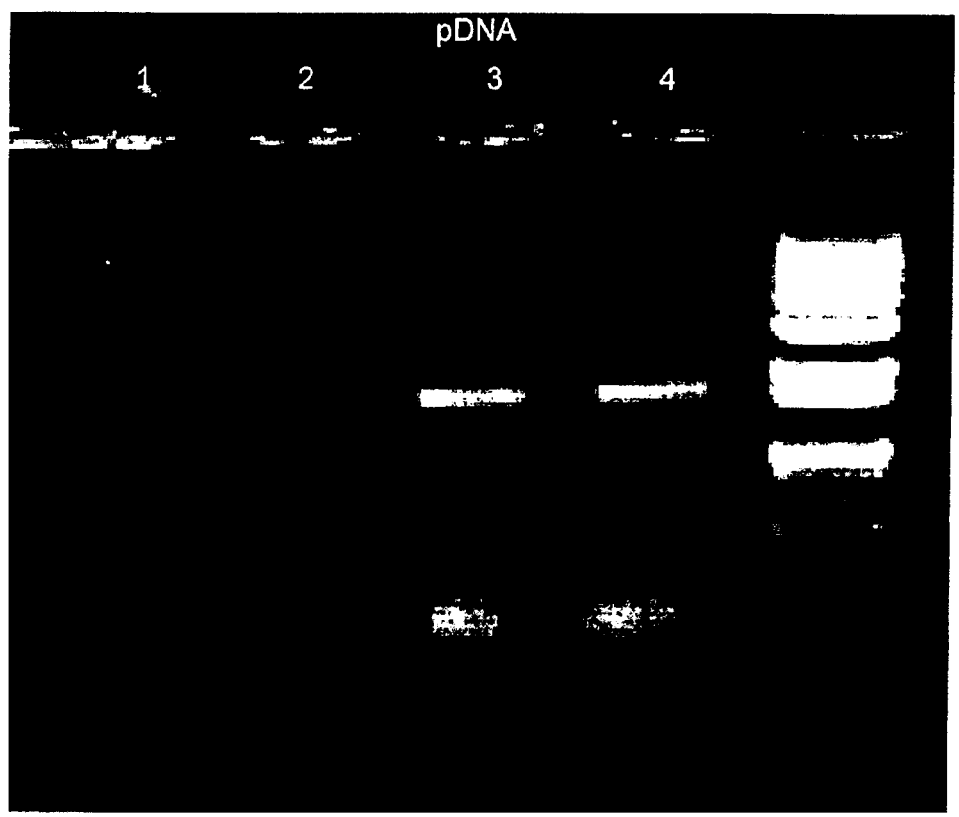
FIG. 4 shows control PCRs for chDNA: negative (water) (lane 1), negative (1×TTE) (lane 2), 1 pg of pDNA and 3 μL 0.6% agarose (lane 3), and 1500 cells (lane 4)

In order to demonstrate the successful application to a standard molecular biology procedure, a mixture of cultured human fibroblasts and purified plasmid DNA was subjected to electrophoresis through an agarose-filled microfluidic chip. In order to verify the presence or absence of either the chDNA or the pDNA in the SR well 1101 and SW well 1102, PCR was used to amplify specific fragments from each, with the PCR products analysed by standard slab gel electrophoresis (FIGS. 2, 3 and 4). As shown in FIG. 2, after the electrophoretic separation stage, the contents collected from SR well 1101 were used for both chDNA-specific PCR (lane 1) and pDNA-specific PCR (lane 5). These positive results verified that pDNA and chDNA were present in the SR well 1101 after the CE stage and had neither been absorbed by the walls, nor fully extracted by the electrophoresis (a negative PCR result might indicate that the CE stage had been continued for too long). The contents collected from SW well 1102 were also used for both chDNA-specific PCR (lane 2) and pDNA-specific PCR (lane 6). The positive result for the pDNA PCR indicates that the pDNA was extracted successfully from the SR well 1101. The negative result from the chDNA PCR indicates that the chDNA was fully trapped by the agarose gel and has not reached the SW well 1102.

The specificity of the PCR reactions were ascertained for each of the plasmid DNA-specific and chromosomal DNA-specific primer pairs (Lane 4 in FIG. 3 and Lane 4 in FIG. 4), and the lack of any contaminating DNA, as evidenced by the lack of bands in both of the water and TTE controls (Lane 1, 2 in FIG. 3 and Lane 1, 2 in FIG. 4). Lane 4 in FIG. 3 demonstrated successful amplification of the COX/1 fragment from a crude lysate of human fibroblasts. An aliquot containing 750 GM01 cells was mixed with an equal volume of distilled water, which automatically lyses the cells by osmotic shock. The cells were left on ice for up to 2 hours until they have been lysed. The necessary PCR reagents were then added directly to the tube, without any subsequent purification or removal of cell debris. As seen in Lane 4 in FIG. 3, the in-tube lysis of 750 cells allows the anticipated fragment to be amplified and demonstrated that contamination from cellular debris does not have a significantly adverse effect on the PCR. Lane 3, FIG. 3 and Lane 3, FIG. 4 show the same cell lysis performed in a tube but in the presence of 3 uL of 0.6% agarose to assure that any agarose left in the wells does not poison both PCRs. By running buffer alone through the chip and adding the spent buffer to the pDNA- and chDNA-specific PCR reaction mixtures, it had been previously ascertained that any pH swings brought about by electrophoresis were adequately controlled and did not adversely affect the PCR outcomes.

Example 2

Separation of Supercoiled DNA

Figure 5:
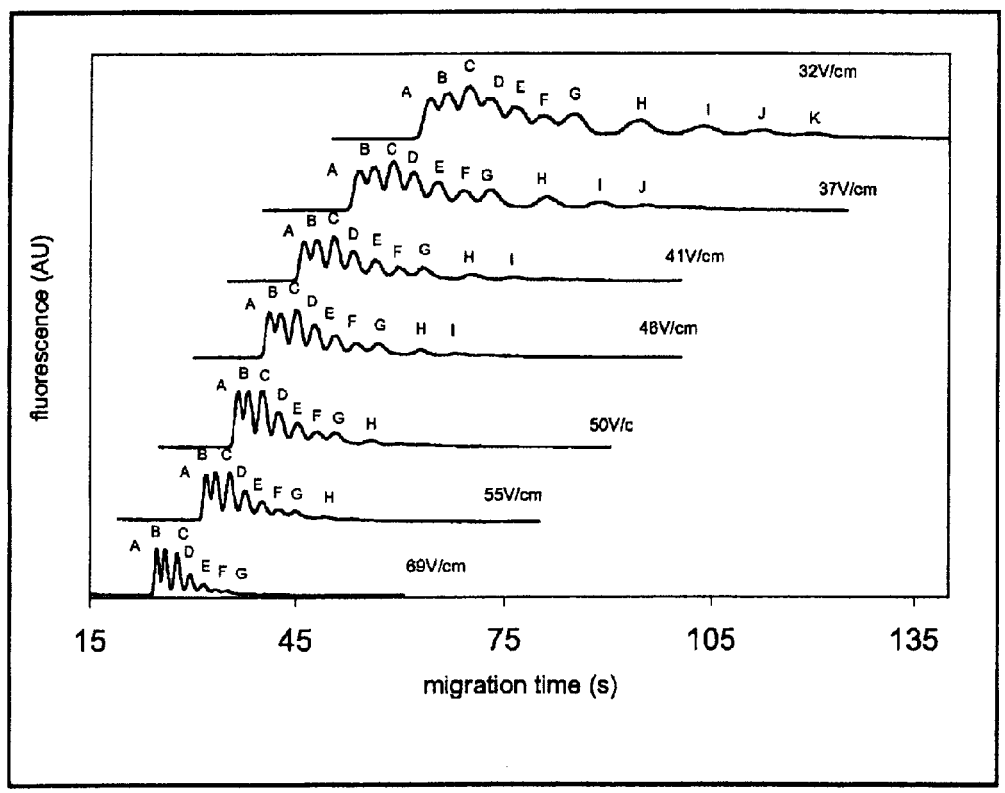
FIG. 5 shows electropherograms of a SC DNA ladder detected at 4 mm under the influence of various applied fields, with plasmid peaks labelled A-K (smallest to largest), performed in 0.6% (w/v) agarose in 1×TTE buffer.
Figure 6:
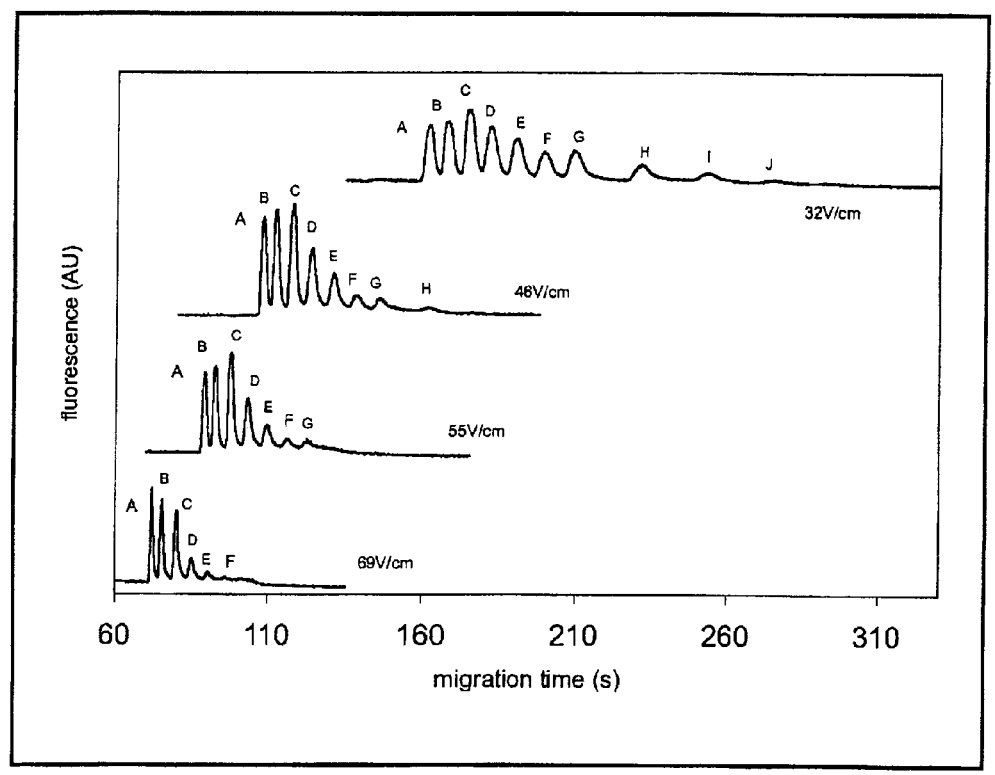
FIG. 6 shows electropherograms of a SC DNA ladder detected at 13 mm under the influence of various applied fields, with plasmid peaks labelled A-K (smallest to largest), performed in 0.6% (w/v) agarose in 1×TTE buffer.

As shown in FIGS. 5 and 6, a standard mixture of SC plasmids was separated, with the resultant electropherograms collected at 4 mm (FIG. 5) and 13 mm (FIG. 6), while varying the electric fields. Similar electropherograms were obtained at 6 mm and 9 mm. As seen in FIG. 5, the separation of the SC DNA ladder at 32 V/cm, with detection at 4 mm, resulted in an approximately 1 kb resolution in the range of 10-14 kb. When the DNA species are detected at 13 mm, the 2-8 kb SC plasmids can be separated with approximately 500 bp resolution while DNA in the 10-14 kb range can be separated with approximately 750 bp resolution. These separations are slower than those that can be obtained with this particular SC ladder and the Agilent 2100 Bioanalyzer using a dilute polymer, but the resolution of the present work is slightly better. As is also evident from FIGS. 5 and 6, as the distance traveled and the electric field increase, the individual DNA species are better separated but the larger DNA is significantly attenuated (often to the point of disappearing).

By comparing electropherograms at various fields and distances, the peaks observed in the electropherogram can be correlated to the known plasmid sizes present in the ladder. The larger-sized SC molecules are absent from the separations over longer distances and subject to higher fields, while the smaller sizes are not resolved over the shorter distances. From the electropherograms shown in FIGS. 5 and 6, the presence or absence of a given size of SC DNA can be used to estimate the critical fields ($E_{crit}$ or $E_c$) that trap a particular size of DNA molecule. For each of the assigned plasmid peaks (A-K), the mobility of the SC plasmid has been calculated, as shown in FIG. 7.

The mobilities of the plasmids were also calculated for the longer detection distances and the mobilities were found to be slightly higher. It is hypothesized, though not necessary to practise the present invention, that this may be a reflection of a relaxation process (the DNA shifting in conformation under the applied field, e.g. as seen in pulsed field methods) or it could be the result of variations in buffer ion concentrations as previously suggested in the art (Slater, G. W. et. al. *Electrophoresis* 23:3791 (2002)) Though not necessary to practise the present invention, it is hypothesized that although the loss of intercalators during the separation could lead to a higher mobility, the degree of labeling for the present application is so low that this effect should be extremely small (less than 1%, since there are so few dye molecules per molecule of DNA). The calculated mobilities, as shown in FIG. 7, can be fitted with a standard model for mobility versus size.

As described above, there have been several different models proposed to explain the behaviour of circular DNA in different gel matrices. As detailed in the art (Akerman, B. et al *Electrophoresis* 23:2549 (2002)), an OC DNA molecule that is impaled upon a trap will need Brownian motion to supply enough energy to move a distance against the electric field in order to free itself. As described by the art, the critical distance is that of the trap length ($L_T$) giving, for the trap energy depth, $U_T$:

$$U_T = N\alpha e L_T E \quad (1)$$

(where N is the number of base pairs, α is the average charge per base pair in units of electron charges (typically~0.1 (Akerman, B. et al *Electrophoresis* 23:2549 (2002))), e is the charge of an electron). Thermal energy will free the molecule from such a trap with a time constant (T) given by the Kramers relation (Akerman, B. et al *Electrophoresis* 23:2549 (2002)):

$$\tau = A\exp(U/kT) \quad (2)$$

(where A is a constant of proportionality, U is as above, k is Boltzmann's constant and T is the absolute temperature). As has been described by others (Akerman, B. et al *Electrophoresis* 23:2549 (2002)), the exponential dependence is such that if U~kT or less, then the DNA is readily freed, whereas if U>5 kT, then the DNA is effectively permanently trapped. This criterion determines a critical field for which U=5 kT.

Example 3

Trapping Capacity of Supercoiled DNA

In order to study the trapping effects, it was ensured that the trapping capacity of the gel matrix was not exceeded. Although the exact amount of DNA injected into the chip is not known, as this is not a well-understood phenomenon, it was found that the DNA in the chip is consumed in a 1000 sec injection. From this, it was possible to estimate the amount of DNA in the injection channel and hence the amount that each separation commences with. Given that the SC ladder contains approximately equal amounts of DNA for each band and that 0.3 μL of the SC ladder (0.25 μg/μl) was loaded, there is approximately 0.007 μg per plasmid band. For a band of about 8 kb (the mid-range of sizes in the ladder), this corresponds to about $8\times10^8$ molecules. Since the injection fully consumes the DNA sample in 1000 sec, this corresponds to an average injection flow of about $8\times10^5$ molecules/sec. At a field strength of 50 V/cm and with the typical mobility of an 8 kb molecule (From FIG. 7, about $1.6\times10^{-3}$, mm-cm/(V-s), this corresponds to about $1\times10^9$ molecules/mm. Since the injection intersection is approximately 100 μm wide, each injection will contain about $1\times10^8$ of the 8 kb molecules. It is known in the art that the distance between traps in agarose was approximately 1 μm and estimated that each trap might absorb as many as 100 loops of DNA, it is presently estimated that a 1 cm long section of the agarose-filled microchannel (100 μm wide and 45 μm deep) would contain $4\times10^7$ traps. Accordingly, these traps would be capable of trapping $4\times10^9$ molecules of DNA and thus can trap 40 times more DNA than in a DNA band being separated. Therefore the presence of any peaks in the chromatograms were the result of a lack of trapping, rather than merely exceeding the trapping capacity of the agarose.

Example 4

Critical Fields for Release of Supercoiled DNA

Figure 8:
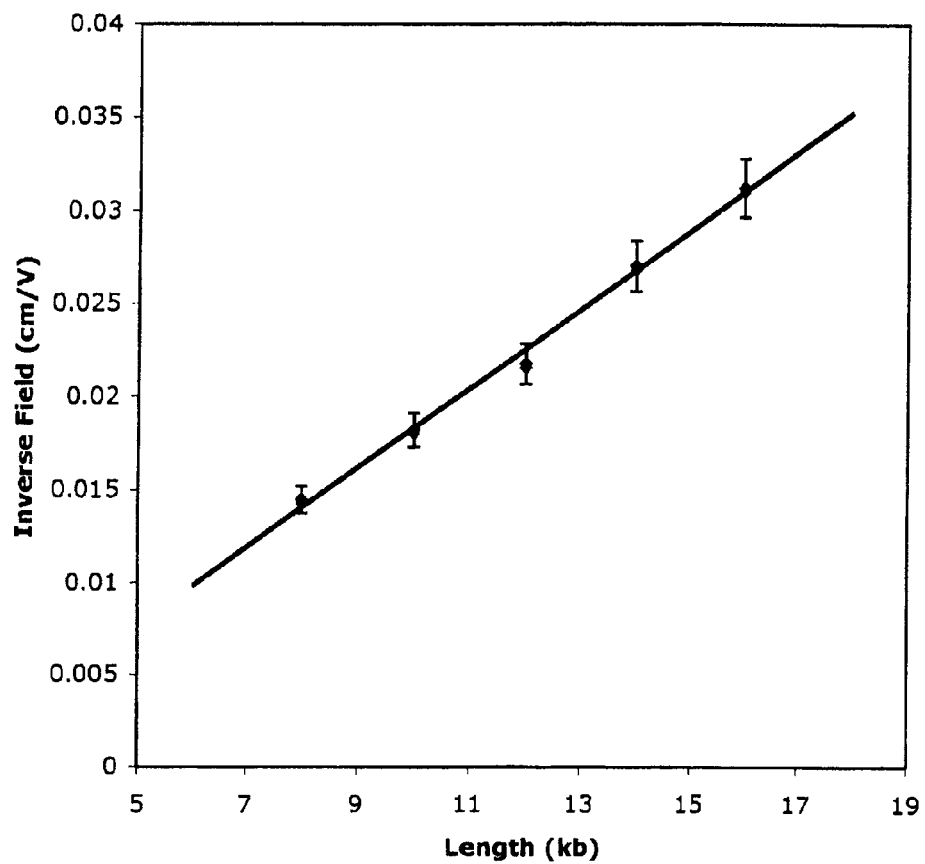
FIG. 8 shows the inverse critical field (cm/V) versus length of SC DNA as detected at a separation distance of 6 mm, with uncertainties in the inverse field estimated at +/−5%.

The actual critical fields ($E_c$) of each plasmid band were determined by the field at which the SC DNA was no longer detectable in our electropherograms at a distance of 6 mm, and plotted the inverse of these values versus the length of the SC DNA. As shown in FIG. 8, the critical field is inversely proportional to the DNA size. At fields above the critical field, and in the limit of low numbers of DNA molecules (so as not to saturate the traps, as discussed above), one would expect the concentration (C) of a given size of DNA to vary with the distance (d) as $C=C_0 \exp(-\beta d)$ where $C_o$ is the initial DNA concentration of that size and β is a parameter that depends on the availability of traps.

In order to show the onset of the trapping near the critical field the data presented in FIGS. 5 and 6 could not be used since the relative peak heights are strongly affected by the injection process (the various sizes enter the injection channel in varying concentrations); as the longer DNA takes longer to arrive at the intersection and the longer DNA is preferentially trapped within the injection channel in a length-dependent fashion. There is also the possibility that trapping within the separation channel (at very short distances) leads to saturation of the traps in the first mm or so. In order to eliminate effects due to uncontrolled mechanisms, the peak height was normalized to the value at 4 mm and the attenuation was observed with distances large enough that trap-saturation could not play a role. Normalization of the peak intensities (peak height of the same plasmid detected at 4 mm) for the larger species of plasmid DNA examined in these experiments and plotting of the intensities versus the distance migrated for different DNA sizes (FIG. 9), typically at two different electric field strengths, further reveals the trapping observed with the larger plasmids. The dominant source of uncertainty for each measurement was the 20% variation in intensity due to uncertainties in optical alignment and focus in moving from one detection location to another. Because of this large uncertainty, it is only meaningful to plot intensity versus distance for the larger DNA sizes (10, 12, 14 and 16 kb) and the higher fields, where trapping led to variations larger than 20%. The transition between the regime of complete trapping (well above the critical field) and that of no detectable trapping (well below the critical field), was very sharp, with only 2 or 3 field strengths showing an intermediate effect (i.e. detectable trapping on a mm-scale). The strong dependence on the electric field strength makes it difficult to identify this exponential behaviour as there are so few data points. For instance, with detection at a separation distance of 4 mm the 16 kb peak was not detectable at or above 46 V/cm (at 6 mm, it was not detectable above 32 V/cm).

Figure 10:
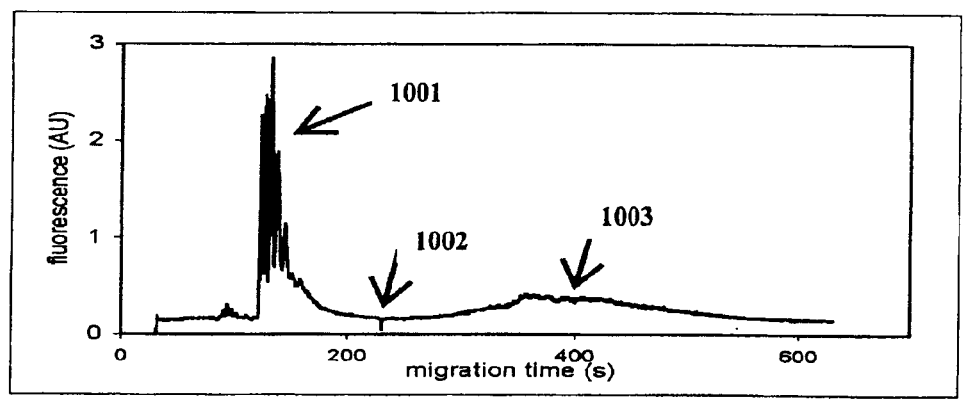
FIG. 10 shows a two-step separation demonstrating the trapping and release of DNA under two distinct voltages.

The basis for such techniques as pulsed-field gel electrophoresis is that trapped DNA can be released by variations in the electric field. As a means of further understanding the mechanisms of trapping observed with SC plasmids, the detrapping effects by varying the electric field across the separation channel of the chip were studied. In order to achieve this variation in electric field, the smaller DNA was separated by trapping the larger DNA through application of a higher field (55 V/cm, detection at 13 mm). The first separation step was considered complete 20 sec after all the peaks had passed the detection spot and the baseline had returned to its original value. A second separation step at 32 V/cm was then performed without pause (FIG. 10), leading to a broad hump 1003 (300 to 500 sec) that is attributed to DNA being released upon lowering of the electric field. As well, SC DNA ladder 1001 is seen, with 1002 representing the point where the voltage was changed from 55 V/cm to 32 V/cm. This behaviour was reproducible over several runs but was not exhibited when the first separation voltage was 32 V/cm. Since the DNA was trapped over a distance of several mm (as seen in FIG. 9.), it is not surprising that individual peaks are not resolved in the released DNA. However, these results demonstrate that the trapping of the SC DNA is reversible.

While particular embodiments of the present invention have been described in the foregoing, it is to be understood that other embodiments are possible within the scope of the invention and are intended to be included herein. It will be clear to any person skilled in the art that modifications of and adjustments to this invention, not shown, are possible without departing from the spirit of the invention as demonstrated through the exemplary embodiments. The invention is therefore to be considered limited solely by the scope of the appended claims.

What is claimed is:

1. A method for isolation of supercoiled nucleic acid of interest contained within a fluid sample containing at least one other contaminating supercoiled nucleic acid of size greater than the supercoiled nucleic acid of interest comprising introducing said fluid sample into a microfluidic capillary containing a trapping matrix at a first position, applying an electric field to the fluid sample such that supercoiled nucleic acid is encouraged to move within said microfluidic capillary containing a trapping matrix to a second position, distal to said first position;

wherein the electric field applied is chosen so as to be greater than the critical electric field for said at least one contaminating nucleic acid, and less than the critical electric field for said supercoiled nucleic acid of interest;

wherein the critical electric field is the minimum electric field required to trap a supercoiled nucleic acid of given size; and wherein the electric field is applied for a period of time sufficient to isolate the supercoiled nucleic acid of interest.

2. The method of claim 1 wherein the fluid sample results from the lysis of a non-eukaryotic or eukaryotic cell.

3. The method of claim 2 wherein the supercoiled nucleic acid of interest is a plasmid.

4. The method of claim 2 wherein fluid sample results from the lysis of a eukaryotic cell and the supercoiled nucleic acid of interest is mitochondrial DNA.

5. The method of claim 4 wherein the trapping matrix is 0.6% agarose in 1X TTE buffer.

6. The method of claim 5 wherein the electric field is less than 35 V/cm.

7. A method for isolation of supercoiled nucleic acid of interest contained within a fluid sample containing at least one other contaminating supercoiled nucleic acid of size less than the supercoiled nucleic acid of interest comprising introducing said fluid sample into a microfluidic capillary containing a trapping matrix at a first position, applying an electric field to the fluid sample such that supercoiled nucleic acid is encouraged to move within said microfluidic capillary containing a trapping matrix to a second position, distal to said first position;

wherein the electric field applied is chosen so as to be less than the critical electric field for said at least one contaminating nucleic acid, and greater than the critical electric field for said supercoiled nucleic acid of interest;

wherein the critical electric field is the minimum electric field required to trap a supercoiled nucleic acid of given size; and wherein the electric field is applied for a period of time sufficient to isolate the supercoiled nucleic acid of interest.

8. The method of claim 7 wherein the fluid sample results from the lysis of a non-eukaryotic or eukaryotic cell.

9. The method of claim 8 wherein the supercoiled nucleic acid of interest is a plasmid.

10. The method of claim 8 wherein fluid sample results from the lysis of a eukaryotic cell and the supercoiled nucleic acid of interest is mitochondrial DNA.

11. The method of claim 10 wherein the trapping matrix is 0.6% agarose in IX TTE buffer.

12. The method of claim 11 wherein the electric field is greater than 35 V/cm.

13. A method for isolation of supercoiled nucleic acid of interest contained within a fluid sample containing at least one other contaminating supercoiled nucleic acid of size less than the supercoiled nucleic acid of interest and at least one other contaminating supercoiled nucleic acid of size greater than the supercoiled nucleic acid of interest comprising introducing said fluid sample into a microfluidic capillary containing a trapping matrix at a first position, applying a first electric field to the fluid sample such that supercoiled nucleic acid is encouraged to move within said microfluidic capillary containing a trapping matrix to a second position, distal to said first position;

applying a second electric field to the fluid sample such that supercoiled nucleic acid is encouraged to move within said microfluidic capillary containing a trapping matrix to a third position, distal to both said first position and second position;

wherein the first electric field applied is chosen so as to be less than the critical electric field for said at least one contaminating nucleic acid of size less than the supercoiled nucleic acid of interest, and greater than the critical electric field for said supercoiled nucleic acid of interest;

wherein the first electric field is applied for a period of time sufficient to isolate the at least one contaminating nucleic acid of size less than supercoiled nucleic acid of interest;

wherein the second electric field applied is chosen so as to be greater than the critical electric field for said at least one contaminating nucleic acid of size greater than the supercoiled nucleic acid of interest, and less than the critical electric field for said supercoiled nucleic acid of interest;

wherein the critical electric field is the minimum electric field required to trap a supercoiled nucleic acid of given size; and wherein the electric field is applied for a period of time sufficient to isolate the supercoiled nucleic acid of interest.

14. The method of claim 13 wherein the fluid sample results from the lysis of a non-eukaryotic or eukaryotic cell.

15. The method of claim 14 wherein the supercoiled nucleic acid of interest is a plasmid.

16. The method of claim 14 wherein fluid sample results from the lysis of a eukaryotic cell and the supercoiled nucleic acid of interest is mitochondrial DNA.

17. The method of claim 16 wherein the trapping matrix is 0.6% agarose in IX TTE buffer.

18. The method of claim 17 wherein the electric field is greater than 35 V/cm.

19. A method for isolation of supercoiled nucleic acid of interest contained within a fluid sample containing at least one other contaminating supercoiled nucleic acid of size less than the supercoiled nucleic acid of interest and at least one other contaminating supercoiled nucleic acid of size greater than the supercoiled nucleic acid of interest comprising introducing said fluid sample into a microfluidic capillary containing a trapping matrix at a first position, applying a first electric field to the fluid sample such that supercoiled nucleic acid is encouraged to move within said microfluidic capillary containing a trapping matrix to a second position, distal to said first position;

applying a second electric field to the fluid sample such that supercoiled nucleic acid is encouraged to move within said microfluidic capillary containing a trapping matrix to a third position, distal to said second position;

wherein the first electric field applied is chosen so as to be greater than the critical electric field for said at least one contaminating nucleic acid of size greater than the supercoiled nucleic acid of interest, and less than the critical electric field for said supercoiled nucleic acid of interest;

wherein the first electric field is applied for a period of time sufficient to isolate the at least one contaminating nucleic acid of size greater than supercoiled nucleic acid of interest;

wherein the second electric field applied is chosen so as to be less than the critical electric field for said at least one contaminating nucleic acid of size less than the supercoiled nucleic acid of interest, and greater than the critical electric field for said supercoiled nucleic acid of interest;

wherein the critical electric field is the minimum electric field required to trap a supercoiled nucleic acid of a given size; and wherein the first electric field is applied for a period of time sufficient to isolate the supercoiled nucleic acid of interest.

20. The method of claim 19 wherein the fluid sample results from the lysis of a non-eukaryotic or eukaryotic cell.

21. The method of claim 20 wherein the supercoiled nucleic acid of interest is a plasmid.

22. The method of claim 21 wherein fluid sample results from the lysis of a eukaryotic cell and the supercoiled nucleic acid of interest is mitochondrial DNA.

23. The method of claim 22 wherein the trapping matrix is 0.6% agarose in IX TTE buffer.

24. The method of claim 23 wherein the electric field is greater than 35 V/cm.

25. A method to isolate supercoiled nucleic acid from chromosomal DNA of size greater than the supercoiled nucleic acid of interest in cells comprising introducing at least the cells into an input well on a microfluidic device in fluid communication with a microfluidic channel—lysing said cells within said input well creating a lysis product electrophoretically transferring said lysis product from the input well to the microfluidic channel applying a electric field to the lysis product such that supercoiled nucleic acid is encouraged to move within said microfluidic capillary containing a trapping matrix;

wherein the electric field applied is chosen so as to be less than the critical electric field for the supercoiled nucleic acid;

wherein the critical electric field is the minimum electric field required to trap a supercoiled nucleic acid molecule of a given size; and wherein the electric field is applied for a period of time sufficient to isolate the supercoiled nucleic acid from the chromosomal DNA.

26. The method of claim 25 wherein the supercoiled nucleic acid is plasmid DNA.

27. The method of claim 25 wherein the supercoiled nucleic acid is mitochondrial DNA.

28. The method of claim 25 where lysis is effected by osmotic shock.

29. A method to isolate supercoiled nucleic acid from chromosomal DNA of size greater than the supercoiled nucleic acid and contaminating non-supercoiled nucleic acids in cells comprising introducing at least the cells into a first input position on a microfluidic device containing at least one input position and at least one output position in fluid communication through at least one microfluidic channel containing a trapping matrix;

lysing said cells within said input well creating a lysis product wherein the electric field is applied for a period of time sufficient to transfer at least the supercoiled nucleic acid from the input position to the output position using at least one microfluidic channel containing a trapping matrix.

30. The method of claim 29 wherein the electric field is between 10 V/cm and 100 V/cm.

31. The method of claim 30 wherein the electric field is 30 V/cm.

32. The method of claim 29 wherein the trapping matrix is 0.6% agarose in IX TTE.

33. A method to isolate supercoiled nucleic acid from chromosomal DNA of size greater than the supercoiled nucleic acid and contaminating non-supercoiled nucleic acids in cells comprising introducing at least the cells into an input well on a microfluidic device containing at least one input well, at least one output well and at least one waste well in fluid communication through at least one microfluidic channel containing a trapping matrix;

lysing said cells within said input well creating a lysis product applying a first electric field such that at least the supercoiled nucleic acid is electrophoretically transferred from the at least one input well to the at least one microfluidic channel;

applying a second electric field to the supercoiled nucleic acid in the microfluidic channel;

applying a third electric field to the supercoiled nucleic acid in the microfluidic channel;

wherein the second electric field applied is chosen so as to be greater than the critical electric field for the supercoiled nucleic acid;

wherein the critical electric field is the minimum electric field required to trap a supercoiled nucleic acid molecule of a given size;

wherein the second electric field is applied for a period of time such that substantially all contaminating non-supercoiled nucleic acids are transferred to the at least one waste well;

wherein the third electric field applied is chosen so as to be less than the critical electric field for the supercoiled nucleic acid; and wherein the third electric field is applied for a period of time sufficient to transfer at least the supercoiled nucleic acid from at least one microfluidic channel to the at least one output well using at least one microfluidic channel.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Saccharomyces cerevisiae

<400> SEQUENCE: 1
tatggatcct tcctttatcg                                              20

<210> SEQ ID NO 2
<211> LENGTH: 20
<212> TYPE: DNA
<213> ORGANISM: Saccharomyces cerevisiae

<400> SEQUENCE: 2
atttaaagct tctcgtaggg                                              20

<210> SEQ ID NO 3
<211> LENGTH: 21
<212> TYPE: DNA
<213> ORGANISM: Homo sapiens

<400> SEQUENCE: 3
aacttggctc caaatggatt a                                            21

<210> SEQ ID NO 4
<211> LENGTH: 22
<212> TYPE: DNA
<213> ORGANISM: Homo sapiens

<400> SEQUENCE: 4
tcctctgaca gtttaagtga tg                                           22